United States Patent [19]

Wood

[11] Patent Number: 4,501,494
[45] Date of Patent: Feb. 26, 1985

[54] APPARATUS FOR DETECTING DEFECTS IN CAPSULE SHELLS

[75] Inventor: Thomas G. Wood, East Brunswick, N.J.

[73] Assignee: E. R. Squibb & Sons, Inc., Princeton, N.J.

[21] Appl. No.: 374,567

[22] Filed: May 3, 1982

[51] Int. Cl.³ ..................... G01N 21/16; G01N 21/32
[52] U.S. Cl. .................................................. 356/240
[58] Field of Search .............. 356/237, 239, 240, 244, 356/64, 66; 209/588; 362/32

[56] References Cited

U.S. PATENT DOCUMENTS

| | | | |
|---|---|---|---|
| 1,000,644 | 8/1911 | Vanneman et al. | 356/64 |
| 1,236,080 | 8/1917 | Hickman | 356/64 |
| 1,361,040 | 12/1920 | Fox | 356/66 |
| 3,709,598 | 1/1973 | Vandenberg et al. | 356/237 |

Primary Examiner—Davis L. Willis
Assistant Examiner—S. A. Turner
Attorney, Agent, or Firm—Lawrence S. Levinson; Burton Rodney

[57] ABSTRACT

Apparatus is provided for use in detecting defects, such as pin holes, cracks and/or uneven gelatin distribution, in capsule shells. The apparatus is comprised of a light box which includes one or a plurality of light bulbs disposed within the box, one or more opaque panels which are disposed in front of each light bulb, and a plurality of transparent pegs carried by the panels and protruding outwardly away from the light bulbs, each peg being adapted to carry a capsule body or cap which fits snugly over the peg. Light shining through the capsule shells disposed on the pegs indicates defects such as pin holes, cracks and/or uneven distribution of gelatin in the capsules.

9 Claims, 4 Drawing Figures

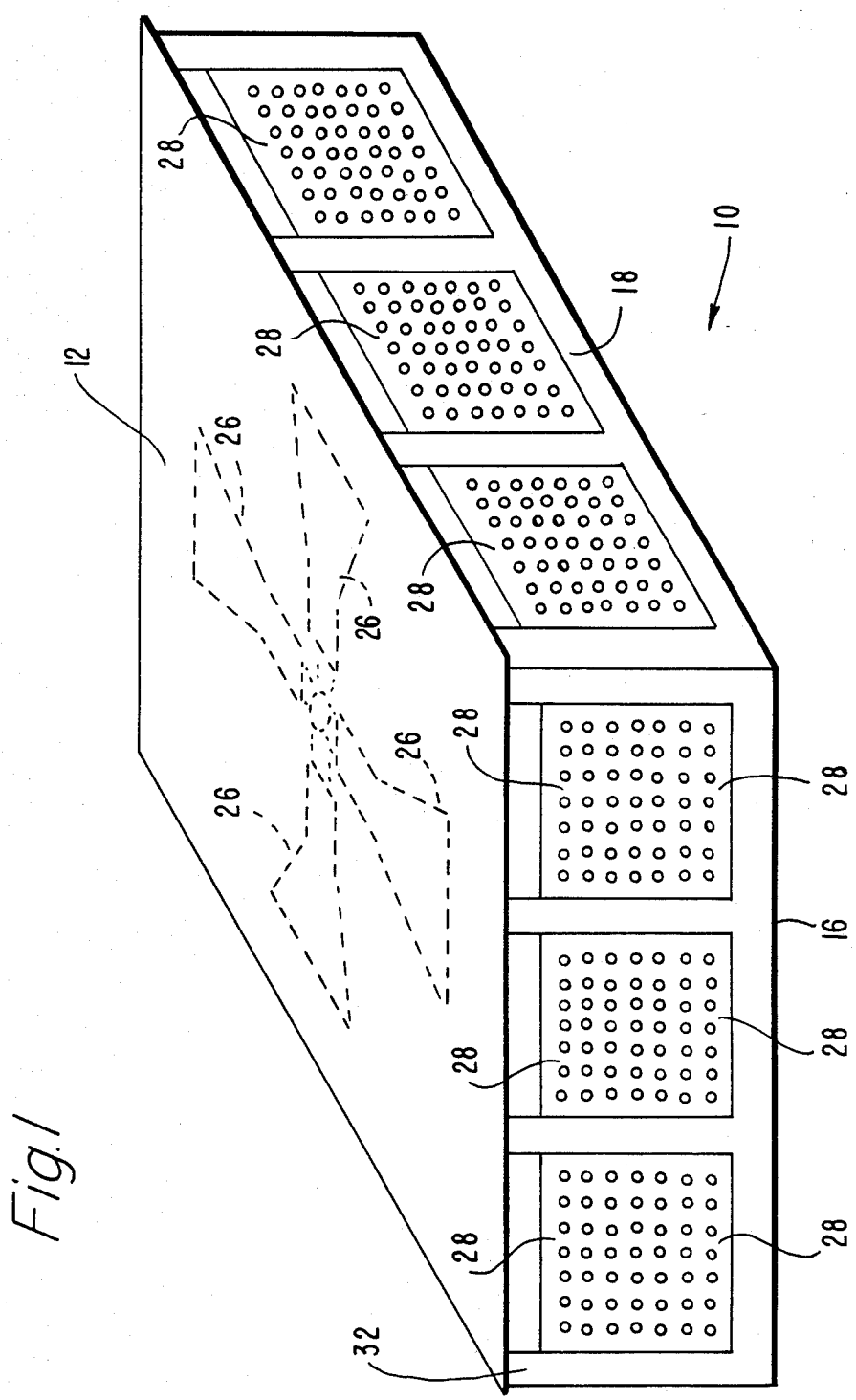

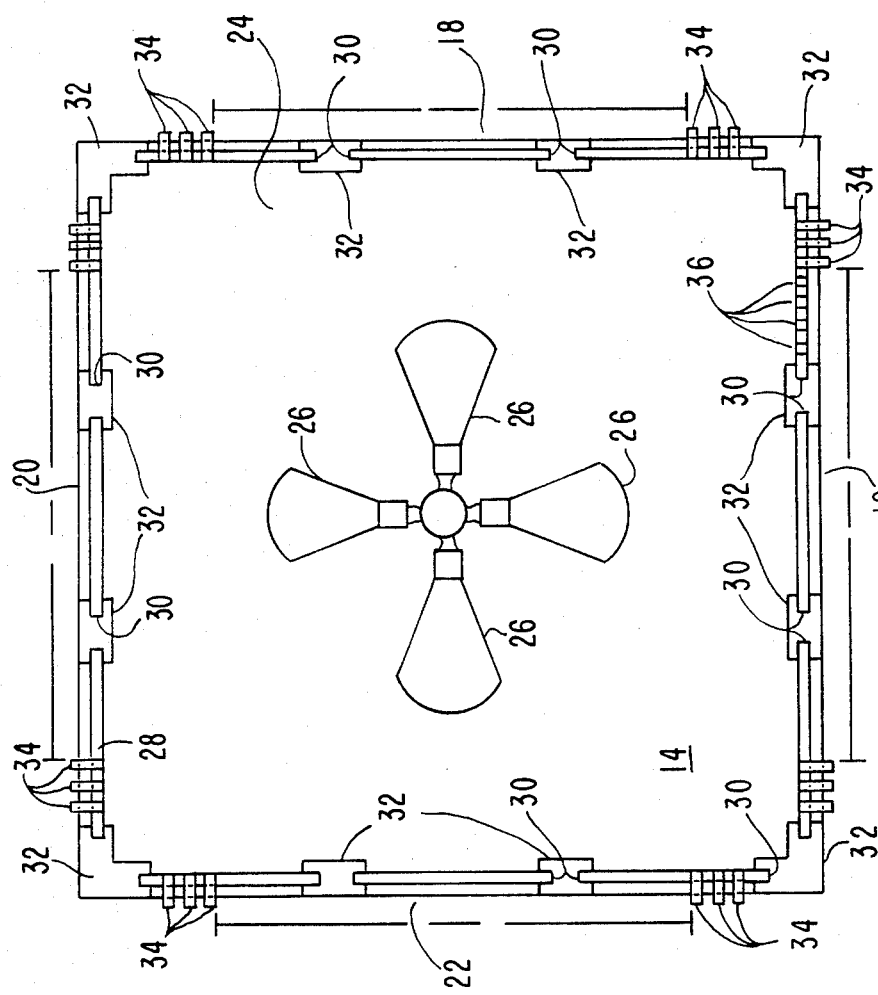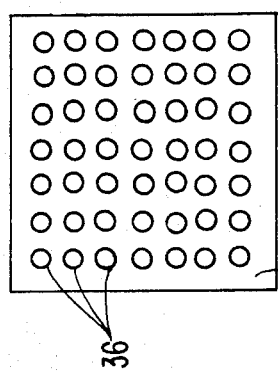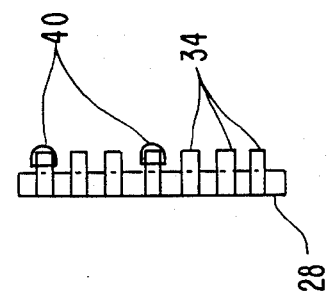

APPARATUS FOR DETECTING DEFECTS IN CAPSULE SHELLS

FIELD OF THE INVENTION

The present invention relates to apparatus for use in detecting defects, such as pin holes, cracks and/or uneven gelatin distribution, in capsule shells.

BACKGROUND OF THE INVENTION

Quality control of capsule bodies and caps is an extremely important matter. Should capsule shells be too brittle they are liable to develop cracks even when subjected to normal wear and tear. The presence of cracks or holes in capsule shells could easily result in leakage and/or spoilage of medication contained in the capsule.

Various quality control tests have been developed by pharmaceutical companies and other manufacturers and vendors of capsule shells for testing for brittleness in empty capsule shells. However, these tests do little for determining if a capsule shell has pin holes or has weakened walls due to uneven gelatin distribution.

BRIEF DESCRIPTION OF THE INVENTION

In accordance with the present invention, apparatus is provided for use in detecting defects, such as pin holes, cracks and/or uneven gelatin distribution, in capsule shells comprising, in combination, a box or other enclosed area which includes three or more sides, and/or rounded or curved surfaces, and a top and bottom defining an internal area, one or more light bulbs or other light source (such as, one or more fiber optic elements) disposed and mounted in the internal area, one or more opaque panels comprising one or more sides of the box, the panels being disposed in front of each light source and a plurality or array of transparent pegs carried by said panels and protruding outwardly away from the light source, each peg being adapted to carry a capsule body or cap which fits snugly over the peg.

Light is shined through each of the pegs and light passes through all of the capsule shells fitted over the pegs showing pin holes, cracks and/or uneven gelatin distribution or other defects in the capsule shells.

BRIEF DESCRIPTION OF THE FIGURES

FIG. 1 is a perspective schematic view of an apparatus in accordance with the present invention including top and bottom portions and four sides which include a series of opaque panels having a plurality of transparent pegs protruding therefrom;

FIG. 2 is a plan view of the apparatus shown in FIG. 1 wherein the top portion has been removed;

FIG. 3 is a plan view of one of the panels shown in FIG. 1 showing openings into which transparent pegs are to be inserted; and FIG. 4 is a side sectional view of one of the panels shown in FIG. 1 including transparent pegs.

DETAILED DESCRIPTION OF THE INVENTION

Referring now to the accompanying Figures wherein like parts are represented by like numerals in the several views, FIG. 1 illustrates a preferred embodiment of the apparatus of the invention generally indicated by the numeral 10 which is specifically designed for detecting pin holes and uneven gelatin distribution in empty capsules. The apparatus 10, as shown, is formed of a box-like structure which includes top portion 12, bottom portion 14, opaque sides 16, 18, 20 and 22, and internal area 24. Mounted in internal area 24, for example, suspended from the top portion 12 or from a conduit disposed in area 24, are a plurality of spot light bulbs 26 which are positioned so as to face the sides 16, 18, 20 and 22 as shown in FIGS. 1 and 2. The light bulbs are connected to a source of current not shown for sake of drawing clarity.

In the embodiment shown, the sides 16, 18, 20 and 22 are formed of a series of opaque panels 28 which slide into tracks or grooves 30 of panel support members 32 as shown so that the panels are positioned in front of light bulbs 26. Each of the opaque panels 28 includes a plurality of transparent pegs 34 which fit into openings 36 in the panels 28 (shown in FIG. 3) and protrude outwardly away from the light sources. The pegs 34 are dimensioned so that gelatin capsule bodies or caps fit snugly over the pegs but so that the capsule shells may be manually rotated on the pegs to facilitate detection of defects in the capsule shells as light is passed through the pegs. Light emitted from bulbs 26 passes through pegs 34 so that if a capsule body or cap 40 positioned on the pegs 34 (as shown in FIG. 4) has pin holes and/or uneven gelatin distribution or other defect, light will pass through the capsule body or cap and such defects will be easily observed.

Where the light source employed generates heat, such as light bulbs or spot lights (as opposed to fiber optic elements which emit cool light), it is important that such heat generating light source be disposed at sufficient distance from the transparent pegs and capsule shells carried thereon to avoid melting of the capsule shells. Thus, for example, where the light source is a 150 watt bulb, the transparent pegs should be maintained at a distance of at least about 4 to 6 inches from the bulb. It will be appreciated that the distance between the light bulb and the pegs will be directly proportional to the wattage of the bulb so that if a 75 watt bulb is employed, the pegs may be disposed at least about 2 to 3 inches from the bulb.

A typical apparatus of the invention will have four sides each of which is 2 to 2.5 feet in length and 0.5 to 1.5 feet in height, two to four removable panels for each side, each of the panels being 0.5 to 0.75 feet square, and pegs which are spaced 0.75 to 1.25 inches from each other on each panel. However, it will be appreciated that any suitable dimensions will come within the scope of the invention.

In the preferred embodiment shown, the panels 28 are opaque and include a network of openings. The transparent pegs are inserted in the openings and are thereby attached to the panels. In another embodiment, the panels, including the pegs, may be cast as a single transparent unit and thereafter, the area of the panels surrounding the pegs may be spray painted or otherwise made opaque while leaving the pegs transparent. The panels are easily removable for loading or unloading of capsule shells. However, the panels may also comprise permanent portions of the apparatus. Different panels containing different size pegs may also be employed depending on the size of the capsule shells to be tested. In addition, the top portion 12 may also be removable for easy access to the panels 28 and light bulbs 26.

It will also be appreciated that the color of the light emitted from the light source should preferably be different from the color of the capsule shells to be tested. Thus, different color light bulbs and/or filters may be employed to produce the color light desired.

What is claimed is:

1. Apparatus for detecting defects in hard gelatin capsule shells comprising, in combination, an enclosed area which is defined by a plurality of external surfaces, a light source which is disposed within the enclosed area, and a plurality of transparent pegs mounted on at least one of said external surfaces and extending outwardly away from the enclosed area and light source, each of said pegs being dimensioned to snugly carry a capsule body or cap, whereby said light source is adapted to emit light which shines through said transparent pegs and capsule shells mounted on said pegs to show up defects in said capsule shells.

2. The apparatus as defined in claim 1 wherein said external surfaces of said apparatus include a top portion and a bottom portion and at least three sides.

3. The apparatus as defined in claim 2 wherein said light source is comprised of a plurality of light bulbs disposed in said enclosed area and positioned to shine light through said transparent pegs.

4. The apparatus as defined in claim 3 wherein said sides comprise a series of panels including a series of bores or openings containing said transparent pegs.

5. The apparatus as defined in claim 4 wherein said panels are removable.

6. The apparatus as defined in claim 3 comprising four opaque sides carrying transparent pegs in each side, and top and bottom portions, and said light source comprises four light bulbs each bulb facing one side.

7. The apparatus as defined in claim 6 wherein each side is comprised of one to four removable opaque panels.

8. The apparatus as defined in claim 2 wherein said sides comprise one or more casted panels including transparent pegs, the area of the panels surrounding said transparent pegs being opaque.

9. A method for detecting defects in capsule shells, which comprises fashioning an apparatus comprising, in combination, an enclosed area which is defined by a plurality of external surfaces, a light source which is disposed within the enclosed area, and a plurality of transparent pegs mounted on at least one of said external surfaces and extending outwardly away from the enclosed area and light source, each of said pegs being dimensioned to snugly carry a capsule body or cap, positioning capsule shells on the transparent pegs, shining light through the transparent pegs and capsule shells mounted thereon and observing if the capsule shells contain defects.

* * * * *